US011084777B2

(12) United States Patent
Savourey et al.

(10) Patent No.: US 11,084,777 B2
(45) Date of Patent: Aug. 10, 2021

(54) METHOD FOR PREPARING ALKYLAMINES

(71) Applicant: Commissariat a l'Energie Atomique et aux Energies Alternatives, Paris (FR)

(72) Inventors: Solène Savourey, Paris (FR); Thibault Cantat, Issy les Moulineaux (FR); Tawfiq Nasr-Allah, Thiais (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 16/083,916

(22) PCT Filed: Mar. 14, 2017

(86) PCT No.: PCT/FR2017/050570
§ 371 (c)(1),
(2) Date: Sep. 11, 2018

(87) PCT Pub. No.: WO2017/158275
PCT Pub. Date: Sep. 21, 2017

(65) Prior Publication Data
US 2019/0084917 A1 Mar. 21, 2019

(30) Foreign Application Priority Data
Mar. 16, 2016 (FR) ...................... 1652230

(51) Int. Cl.
*C07D 217/04* (2006.01)
*C07C 209/68* (2006.01)
(52) U.S. Cl.
CPC .......... *C07C 209/68* (2013.01); *C07D 217/04* (2013.01)

(58) Field of Classification Search
CPC ............................ C07C 209/68; C07D 217/04
USPC ......................................................... 546/150
See application file for complete search history.

(56) References Cited

FOREIGN PATENT DOCUMENTS

EP 2821397 A1 1/2015

OTHER PUBLICATIONS

Hawley, The Condensed Chemical Dictionary, 8th ed., 1971, p. 170. (Year: 1971).*
International Search Report issued in corresponding International Patent Application No. PCT/FR2017/050570 dated Jun. 6, 2017.
Yang et al., "B(C6F5)3-catalyzed methylation of amines using CO2 as a C1 building block," Green Chemistry, 17: 4189-4193 (2015).
(Continued)

*Primary Examiner* — Taylor V Oh
(74) *Attorney, Agent, or Firm* — Morgan, Lewis & Bockius LLP

(57) ABSTRACT

The present invention relates to a method for preparing alkylamines using carbon monoxide and the use of this method in the manufacturing of vitamins, pharmaceutical products, adhesives, acrylic fibres and synthetic leathers, pesticides, surfactants, detergents and fertilisers.
It also relates to a method for manufacturing vitamins, pharmaceutical products, adhesives, acrylic fibres, synthetic leathers, pesticides, surfactants, detergents and fertilisers, comprising a step of preparing alkylamines by the method according to the invention.
The present invention further relates to a method for preparing marked alkylamines and uses thereof.

18 Claims, 1 Drawing Sheet

(56) References Cited

OTHER PUBLICATIONS

Gonzalez-Sebastian et al., "Selective N-Methylation of Aliphatic Amines with CO2 and Hydrosilanes Using Nickel-Phosphine Catalysts," Organometallics, 34: 763-769 (2015).

Dombray et al., "Cobalt Carbonyl-Based Catalyst for Hydrosilylation of Carboxamides," Advanced Synthesis & Catalysis, 355: 3358-3362 (2013).

* cited by examiner

METHOD FOR PREPARING ALKYLAMINES

The present invention relates to a method for preparing alkylamines using carbon monoxide and the use of this method in the manufacturing of vitamins, pharmaceutical products, adhesives, acrylic fibres and synthetic leathers, pesticides, surfactants, detergents and fertilisers.

It also relates to a method for manufacturing vitamins, pharmaceutical products, adhesives, acrylic fibres, synthetic leathers, pesticides, surfactants, detergents and fertilisers, comprising a step for preparing alkylamines by the method according to the invention.

The present invention further relates to a method for preparing marked alkylamines and uses thereof.

Amines are basic chemical products. They are in particular used as dyes or medications. To date, methylamines can be synthesised in a "sustainable" way from $CO_2$, whereas alkylamines are synthesised from petrochemical derivatives.

One of the main synthetic route of alkylamines is alkylation of amines using alcohols or haloalkanes (FIG. 1) that are themselves produced in several steps from petroleum or from carbon monoxide (CO) and hydrogen ($H_2$) via the Fischer-Tropsch process. The major drawback of this synthesis route is the presence of multiple steps which result in low yields and high processing and separation costs.

One of the other main routes for synthesising alkylamines is the reduction of amides. This can be carried out by hydrogenation of amides with, however, limited efficiency and high sensitivity to the nature of the amide. The hydrogenation can be carried out by hydrosilylation as shown in FIG. 2, or by hydroboration, two techniques that have good yields but low economy of atoms. For example, the hydrosilylation of amides in the presence of $Co_2CO_8$ as a catalyst (T. Dombray, C. Helleu, C. Darcel, J. Sortais, *Adv. Synth. Catal.*, 2013, 355, 3358) may have quantitative yields but will be effective only with aromatic amides. In addition, the substituent number on the nitrogen atom of the amides and the steric hindrance that results therefrom may have an influence on the reactivity and the speed of reduction of the amide.

Moreover, the synthesis methods described above involve several steps that require intermediate purifications.

The use of CO valuable as a carbon source for producing chemical consumables is a major challenge for reducing our dependency on fossil fuels. In addition, CO may be considered to be a renewable carbon source since it can be produced now from biomass or $CO_2$. The technical difficulty lies in the development of chemical reactions that make it possible to functionalise the CO while reducing the carbonated centre (i.e. by replacing the C—O bond of the CO with C—H or C—C bonds).

The conversion of CO into chemical consumables such as alkylamines is therefore of a special interest.

In the context of the synthesis of alkylamines using carbon monoxide, the technical challenge is to couple the functionalization of the carbon monoxide (formation of a C—N bond) with a chemical reduction step (formation of two C—H bonds) in order to obtain alkylamines having variable chain lengths. To maximise the energy efficiency of such a transformation, it is necessary to develop reactions with a limited number of steps (ideally only one) and that are catalysed, in order to avoid energy losses of a kinetic type.

Therefore, there is a real need for a method for the sustainable preparation of alkylamines with different chain lengths.

In particular, there is a real need for a method capable of preparing alkylamines using carbon monoxide (CO) as a renewable molecular brick leading to the formation of alkyl chains whose length may vary, said method being capable of coupling the functionalization of the carbon monoxide with a chemical reduction step.

More particularly, there is a real need for a method capable of obtaining, in a limited number of steps or even in a single step, alkyl amines wherein the length of the alkyl chains may vary in a controlled manner from a renewable carbon source.

Moreover, marked alkylamines, incorporating radioisotopes and/or stable isotopes, have a particular interest in numerous fields such as, for example, in life sciences (study/elucidation of enzymatic mechanisms, biosynthetic mechanisms, in biochemistry, etc.), environmental sciences (tracing of waste, etc.), research (study/elucidation of reaction mechanisms) or research and development of novel pharmaceutical and therapeutic products. Thus, developing a method as described above for preparing marked alkylamines, meeting the requirements indicated above, addresses a real need.

The aim of the present invention is precisely to meet these requirements by providing a method for preparing alkylamines of formula (I):

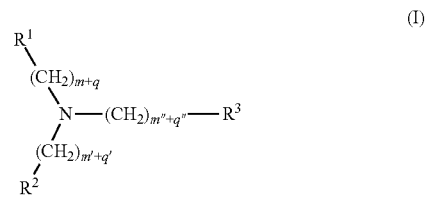

wherein:
- $R^1$, $R^2$ and $R^3$ represent, independently of each other, a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted; or
- $R^1$ and $R^2$, taken together with the nitrogen atom to which they are bound, form a heterocycle, optionally substituted, and
- $R^3$ represents a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted;
- m, m', m" are integers chosen from 0 and 1
- q, q', q" are integers chosen from 0, 1, 2, 3, 4, 5, 6, 7, 8, 9 and 10;
- $R^1$, $R^2$ and $R^3$ and —$CH_2$— optionally comprise H, C, N, O, F, Si and/or S as defined below:
- H represents a hydrogen atom ($^1H$), deuterium ($^2H$) or tritium ($^3H$);
- C represents a carbon atom ($^{12}C$), an isotope $^{11}C$, $^{13}C$ or $^{14}C$;
- N represents a nitrogen atom ($^{14}N$), an isotope $^{15}N$;
- O represents an oxygen atom ($^{16}O$), an isotope $^{17}O$ or $^{18}O$;
- F represents a fluorine atom ($^{19}F$), an isotope $^{18}F$;
- S represents a sulphur atom ($^{32}S$), an isotope $^{33}S$, $^{34}S$ or $^{36}S$;

characterised by reacting an amine of formula (II)

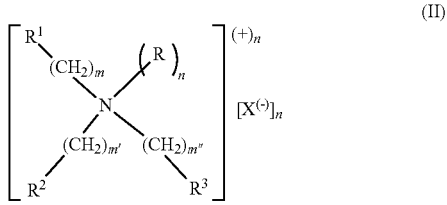

wherein
- $R^1$, $R^2$ and $R^3$, —$CH_2$—, m, m' and m" are as defined above;
- R represents a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted;
- X represents a halogen atom, trifluoromethylsulfonate (triflate), methanesulfonate (mesylate), p-toluenesulfonic acid (tosylate);
- n is an integer chosen from 0 and 1;

with CO wherein C and O are as defined above and a reducing agent chosen from $H_2$, $LiAlH_4$, $NaBH_4$, Zn, $LiBH_4$,
a silane of formula (III)

and
a borane of formula (IV)

wherein
- $R^4$, $R^5$, $R^6$, $R^7$ and $R^8$ represent, independently of each other, a hydrogen atom, an alkyl group, an alkoxy group, an alkenyl group, an alkynyl group, an aryl group, a heteroaryl group, a heterocycle, a silyl group, a siloxy group or an amino group, said alkyl, alkenyl, alkynyl, aryl, heteroaryl, heterocycle, silyl, siloxy and amino groups being optionally substituted; or
- $R^7$ and $R^8$, taken together with the boron atom to which they are bound, form an optionally substituted heterocycle;

in the presence of a metal catalyst chosen from metal salts and complexes, and optionally a promoter.

Thus, with the method of the invention alkylamines of formula (I) that are both non-marked and marked can be prepared.

The method of the invention has the advantage of making it possible to convert CO into alkylamines with a wide choice of amines of formula (II) (primary, secondary, aromatic, aliphatic amines, etc.). This method makes it possible to create one or more alkyl chains on the amines of formula (II) and/or to lengthen the alkyl chain or chains already present on the amines of formula (II), which so far has never been disclosed. In this method, the CO, by virtue of the presence of reducing agents that reduce CO, under catalytic conditions, is used to alkylate said amines of formula (II).

Another advantage of the method of the invention is that it makes it possible, when desired, to promote the obtaining of certain types of alkylamines of formula (I) from the amine of formula (II).

As indicated above, the method of the invention makes it possible to obtain the alkylamines of formula (I) in a limited number of steps (one or two steps) without separation of the intermediate products.

Thus, the preparation of alkylamines using the method of the invention, in one or two steps, is a one-pot synthesis, that is to say that the amines of formula (II) are transformed into alkylamines of formula (I) by undergoing several successive and/or simultaneous reactions in a single reaction mixture (a single reactor for example), and therefore avoiding long processes of separation and purification of the intermediate compounds. Thus, on an industrial level, the method of the invention is very interesting since it makes it possible to save time and production costs and to gain in global efficiency.

For the method of the invention to allow obtaining alkylamines of formula (I), a judicious and appropriate combination of amines of formula (II), reducing agent, catalysts and optionally promoters is essential. It is, in particular, necessary, in choosing the amine of formula (II) and the catalyst, to take account in particular of their respective steric hindrances, the reducing character of the reducing agent, the nucleophilic character of the catalyst, and their solubility in the reaction medium.

Without being bound by the theory, in the method of the invention the technical challenge is to couple the functionalization of the carbon monoxide (formation of a C—N bond) with a chemical reduction step (formation of two C—H bonds), which a priori is neither obvious nor easy. Indeed, it is not enough that the carbonylation followed by the reduction take place independently, but the carbonylation must be able to take place in the presence of a reducing agent and the reduction must be able to take place in the presence of CO, and this at the appropriate time and under the same conditions. Yet, for example, silanes (reducing agent) are known for forming methane in the presence of iodomethane (promoter), which would deactivate the system, or for forming a silylated amine in the presence of an amine as shown in FIG. 3. The inventors found, entirely unexpectedly, that a judicious choice of reagents and operating conditions makes it possible to eliminate undesirable reactions. Moreover, a judicious choice of reagents and operating conditions makes it possible to effect either a single or a cascade of a plurality of carbonylations and reductions, thus leading to the formation of a plurality of C—C bonds.

Within the meaning of the invention, a "promoter" refers to a compound that increases the catalytic power of a catalyst, without itself having any intrinsic catalytic power. The promoters are by themselves inactive.

The promoters may be of formula RX, wherein
- R represents a hydrogen atom, an alkyl group, an alkenyl group, an alkynyl group, an aryl group, a heteroaryl group, a heterocycle, said alkyl, alkenyl, alkynyl, heteroaryl, heterocycle groups being optionally substituted; with the alkyl, alkenyl, alkynyl, heteroaryl, heterocycle groups as defined in the context of the present invention; and X represents a halogen atom chosen from fluorine, chlorine, bromine and iodine atoms; tifluoromethylsulfonate (triflate), methanesulfonate (mesylate) and p-toluenesulfonic acid (tosylate).

The promoters may also be a quaternary ammonium salt of formula $R_9R^{10}R_{11}R_{12}NX$ wherein $R_9$, $R_{10}$, $R_{11}$, $R_{12}$ represent, independently of each other, a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted; with the alkyl, alkenyl, alkynyl, aryl, heteroaryl, heterocycle groups as defined in the context of the present invention; and X represents a halogen atom chosen from fluorine, chlorine, bromine and iodine atoms; tifluoromethylsulfonate (triflate), methanesulfonate (mesylate) and p-toluenesulfonic acid (tosylate).

"Catalyst", within the meaning of the invention, means a compound capable of modifying, in particular by increasing, the speed of the chemical reaction in which it participates, and which is regenerated at the end of the reaction. This definition encompasses both catalysts, that is to say compounds that exert their catalytic activity without needing to undergo any modification or conversion, and the compounds (also referred to as pre-catalysts) that are introduced into the reaction medium and that are converted therein into a catalyst.

In the context of the invention, "additive" means a compound able to improve and increase the yield and/or speed of the conversion of the amines of formula (II) into alkylamines of formula (I), but which, alone, is not able to catalyse this conversion. Additives may be chosen from amides, preferably aromatic, or derivatives, in particular acetanilide, benzanilide and N-methylacetanilide; and Lewis acids, in particular $AlCl_3$, $LiCl$, $LiBF_4$, $FeCl_3$, $InCl_3$, $BiCl_3$.

Within the meaning of the present invention, an "alkyl" group describes a carbon radical, linear, branched or cyclic, saturated, optionally substituted, comprising 1 to 12 carbon atoms. As saturated alkyl, linear or branched, mention can be made for example of methyl, ethyl, propyl, butyl, pentyl, hexyl, octyl, nonyl, decyl, undecyl, dodecanyl radicals and the branched isomers thereof. As cyclic alkyl, mention can be made of cyclopropyl, cyclobutyl, cyclopentyl, cyclohexyl, cycloheptyl, cyclooctyl, bicyclo[2,1,1] hexyl, bicyclo [2,2,1] heptyl radicals. The alkyl group may comprise for example 1 to 8 carbon atoms.

"Alkenyl" or "alkynyl" means an unsaturated carbon radical, linear, branched or cyclic, optionally substituted, said unsaturated carbon radical comprising 2 to 12 carbon atoms comprising at least one double bond (alkenyl) or one triple bond (alkynyl). In this regard, mention can be made, for example, of the ethylenyl, propylenyl, butenyl, pentenyl, hexenyl, actylenyl, propynyl, butynyl, pentynyl and hexynyl radicals and the branched isomers thereof. As cyclic alkenyls, mention can be made for example of cyclopentenyl and cyclohexenyl. The alkenyl and alkynyl groups may comprise for example 2 to 8 carbon atoms.

The alkyl, alkenyl and alkynyl groups may optionally be substituted by one or more hydroxyl groups; one or more alkoxy groups; one or more halogen atoms chosen from fluorine, chlorine, bromine or iodine atoms; one or more nitro groups ($—NO_2$); one or more nitrile groups (—CN); one or more aryl groups, with the alkoxy and aryl groups as defined in the context of the present invention.

The term "aryl" refers in general terms to a cyclic aromatic substituent comprising 6 to 20 carbon atoms. In the context of the invention the aryl group may be mono- or polycyclic. The aryl group may optionally be substituted by one or more hydroxyl groups, one or more alkoxy groups, one or more "siloxy" groups, one or more halogen atoms chosen from fluorine, chlorine, bromine and iodine atoms, one or more nitro groups ($—NO_2$), one or more nitrile groups (—CN), one or more alkyl groups, with the alkoxy, alkyl and siloxy groups as defined in the context of the present invention. The aryl group may for example comprise 6 to 10 carbon atoms. By way of indication, mention can be made of phenyl, benzyl, naphthyl, o-toluyl, m-toluyl, p-nitrophenyl, o-methoxyphenyl, m-methoxyphenyl and p-methoxyphenyl, o-methoxybenzyl, p-methoxybenzyl, m-methoxybenzyl, o-methylbenzyl, p-methylbenzyl and m-methylbenzyl groups.

The term «heteroaryl» refers in general terms to a mono- or polycyclic aromatic substituent comprising 5 to 12 members, including at least 2 carbon atoms, and at least one heteroatom chosen from nitrogen, oxygen or sulphur. By way of indication, mention can be made of furyl, benzofuranyl, pyrrolyl, indolyl, isoindolyl, azaindolyl, thiophenyl, benzothiophenyl, pyridyl, quinolinyl, isoquinolinyl, imidazolyl, benzimidazolyl, triazolyl, pyrazolyl, oxazolyl, isoxazolyl, benzoxazolyl, thiazolyl, benzothiazolyl, isothiazolyl, pyridazinyl, pyrimidilyl, pyrimidinyl, pyrazinyl, triazinyl, cinnolinyl, phthalazinyl, quinazolinyl 1,1-diphenylhydrazinyl, 1,2-diphenylhydrazinyl, carbazolyl groups. The heteroaryl group may optionally be substituted by one or more hydroxyl groups, one or more alkoxy groups, one or more halogen atoms chosen from fluorine, chlorine, bromine and iodine atoms, one or more nitro groups ($—NO_2$), one or more nitrile groups (—CN), one or more aryl groups, one or more alkyl groups, with the alkyl, alkoxy and aryl groups as defined in the context of the present invention. It is obvious that the term "heteroaryl" also encompasses the mono- or polycyclic aromatic compounds comprising 5 to 12 members, including at least 2 carbon atoms, and at least one heteroatom chosen from nitrogen, oxygen or sulphur, from which the aforementioned radicals/groups derive.

The term "alkoxy" means an alkyl group, as defined above, bound by an oxygen atom (—O-alkyl).

The term "heterocycle" or "heterocyclic" designates in general terms a mono- or polycyclic substituent comprising 5 to 12 members, saturated or unsaturated, containing 1 to 4 heteroatoms chosen independently of each other, from nitrogen, oxygen, boron and sulphur. By way of indication, mention can be made of borolan, borol, borinan, 9-borabicyclo[3.3.1]nonane (9-BBN), 1,3,2-benzodioxaborol (catecholborane or catBH), pinacolborane (pinBH); the substituents morpholinyl, piperidinyl, piperazinyl, pyrrolidinyl, imidazolyl, imidazolidinyl, imidazolinyl, pyrazolidinyl, tetrahydrofuranyl, tetrahydropyranyl, tetrahydropyrimidinyl, tetrahydroisoquinoleinyl, benzazepinyl, triazolyl, pyrazolyl, thianyl, oxazolidinyl, isoxazolidinyl, thiazolidinyl, isothiazolidinyl. The heterocycle may optionally be substituted by one or more hydroxyl groups, one or more alkoxy groups, one or more aryl groups, one or more halogen atoms chosen from fluorine, chlorine, bromine and iodine atoms, one or more nitro groups ($—NO_2$), one or more nitrile groups (—CN), one or more alkyl groups, with the alkyl, alkoxy and aryl groups as defined in the context of the present invention. It is obvious that the term "heterocycle" or "heterocyclic" also encompasses the mono- or polycyclic compounds, comprising 5 to 12 members, saturated or unsaturated, containing 1 to 4 heteroatoms chosen independently of each other, from nitrogen, oxygen, boron and sulphur, from which the aforementioned radicals/groups derive.

"Halogen" atom means an atom chosen from fluorine, chlorine, bromine and iodine atoms.

"Silyl" group means a group of formula [—Si(Y)$_3$] wherein each Y, independently of each other, is chosen from a hydrogen atom; one or more halogen atoms chosen from fluorine, chlorine, bromine or iodine atoms; one or more alkyl groups; one or more alkoxy groups; one or more siloxy groups; one or more aryl groups; with the alkyl, alkoxy and aryl groups as defined in the context of the present invention. In this regard mention can be made, for example, of trimethylsilyl (TMS), triethylsilyl ((CH$_3$CH$_2$)$_3$Si— or TES), tert-butyldiphenylsilyl (TBDPS), tert-butyldimethylsilyl (TBS/TBDMS), dimethylhydrosilyl, triisopropylsilyl (TIPS), tri(trimethylsilyl)silyl or ((CH$_3$)$_3$Si)$_3$Si-(TTMS), tri (tert-butyl)silyl or ((CH$_3$)$_3$C)$_3$Si—, (C$_6$H$_5$)H$_2$Si—, diphenylhydrosilyl ((C$_6$H$_5$)$_2$HSi—), triphenylsilyl ((C$_6$H$_5$)$_3$Si—), triethoxysilyl ((EtO)$_3$Si—). It is obvious that the term "silyl" also encompasses the compounds from which the aforementioned radicals/groups derive.

"Siloxy" group means a silyl group, as defined above, bound by an oxygen atom (—O—Si(Y)$_3$) with Y as defined above. In this regard mention can be made for example of trimethylsiloxy —OSi(CH$_3$)$_3$, triethylsiloxy —OSi(CH$_2$CH$_3$)$_3$, tert-butyldiphenylsiloxy —OSi(tBuPh$_2$)$_3$, methylsiloxy (—OSi(H)$_2$(CH$_3$), dimethylsiloxy (—OSi(H)(CH$_3$)$_2$), ethylsiloxy (—OSi(H)$_2$(C$_2$H$_5$), diethylsiloxy (—OSi(H)(C$_2$H$_5$)$_2$), tetramethyldisiloxane (TMDS or O(Si(Me)$_2$H)$_2$). In the context of the invention, the siloxy group also encompasses polymeric siloxys. In this regard mention can be made for example of polymethylhydrosiloxane (PMHS), polydimethylsiloxane, poly(dimethylsiloxane-co-diphenylsiloxane). It is obvious that the term "siloxy" also encompasses the compounds from which the aforementioned radicals/groups derive.

"Amino" group means a group of formula —NR$^{13}$R$^{14}$, wherein: R$^{13}$ and R$^{14}$ represent, independently of each other, a hydrogen atom, an alkyl group, an alkenyl group, an alkynyl group, an aryl group, a heteroaryl group, a heterocycle, a silyl group, a siloxy group, with the alkyl, alkenyl, alkynyl, aryl, heteroaryl, heterocycle, silyl and siloxy groups as defined in the context of the present invention; or R$^{13}$ and R$^{14}$, taken together with the nitrogen atom to which they are bound, form a heterocycle optionally substituted by one or more hydroxyl groups; one or more alkyl groups, one or more alkoxy groups; one or more halogen atoms chosen from fluorine, chlorine, bromine and iodine atoms; one or more nitro groups (—NO$_2$); one or more nitrile groups (—CN); one or more aryl groups; with the alkyl, alkoxy and aryl groups as defined in the context of the present invention. It is obvious that the term "amino" also encompasses the compounds from which the aforementioned radicals/groups derive. In this regard, mention can be made for example of diethylamino (—NEt$_2$), diphenylamino (—NPh$_2$), methylethylamino (—NMeEt), bis(trimethylsilyl)amino (—N(SiCH$_3$)$_2$) and N-methylaniline (—N(Me)(Ph)).

Generally, the definitions of the various radicals/groups produced in the context of the present invention also encompass the compounds from which the aforementioned radicals/groups derive.

The substituents, radicals and groups defined above may comprise, optionally, deuterium ($^2$H), tritium ($^3$H), $^{11}$C, $^{13}$C, 14C, $^{15}$N, $^{17}$O, $^{18}$O, $^{18}$F, $^{33}$S, $^{34}$S and/or $^{36}$S.

When the compounds of formula (I), (II) comprise at least a radiomarker/radiotracer or an isotope, they may also be designated by the formulae (I'), (II') and (III').

According to a first embodiment of the invention,

R$^1$, R$^2$ and R$^3$ represent, independently of each other, a hydrogen atom, an alkyl group, an aryl group, a heteroaryl group, a heterocycle, said alkyl, aryl, heteroaryl, heterocycle groups being optionally substituted;

m, m' and m" are integers chosen from 0 and 1;

q, q', q" are integers chosen from 0, 1, 2, 3, 4, 5, 6, 7, 8, 9 and 10;

n=0.

In this embodiment, preferably:

R$^1$, R$^2$ and R$^3$ represent, independently of each other, a hydrogen atom; an alkyl group chosen from methyl, ethyl, propyl, butyl, pentyl, hexyl, heptyl groups and the branched isomers thereof; an aryl group, optionally substituted, chosen from benzyl, phenyl, o-toluyl, m-toluyl, p-nitrophenyl, o-methoxyphenyl, m-methoxyphenyl and p-methoxyphenyl, o-methoxybenzyl, p-methoxybenzyl, m-methoxybenzyl, o-methylbenzyl, p-methylbenzyl and m-methylbenzyl.

In this first embodiment, the presence of a promoter and/or of an additive may be advantageous.

According to a second embodiment of the invention:

R$^1$ and R$^2$, taken together with the nitrogen atom to which they are bound, form a heterocycle, optionally substituted, and R$^3$ represents a hydrogen atom, an alkyl group, an aryl group, a heteroaryl group, a heterocycle, said alkyl, aryl, heteroaryl, heterocycle groups being optionally substituted;

m, m' and m" are integers chosen from 0 and 1;

q, q', q" are integers chosen from 0, 1, 2, 3, 4, 5, 6, 7, 8, 9 and 10;

n=0.

In this embodiment, preferably:

R$^1$ and R$^2$, taken together with the nitrogen atom to which they are bound, form a heterocycle, optionally substituted, chosen from morpholine, piperidine, piperazine, pyrrolidine and tetrahydroisoquinoline, indoline and isoindoline, and R$^3$ represents a hydrogen atom; an alkyl group chosen from methyl, ethyl, propyl, butyl, pentyl, hexyl, heptyl groups, and the branched isomers thereof; an aryl group, optionally substituted, chosen from benzyl, phenyl, o-toluyl, m-toluyl, p-nitrophenyl, o-methoxyphenyl, m-methoxyphenyl and p-methoxyphenyl, o-methoxybenzyl, p-methoxybenzyl, m-methoxybenzyl, o-methylbenzyl, p-methylbenzyl and m-methylbenzyl.

In this second embodiment, the presence of a promoter and/or of an additive may be advantageous.

According to a third embodiment of the invention:

R$^1$, R$^2$ and R$^3$ represent, independently of each other, a hydrogen atom, an alkyl group, an aryl group, a heteroaryl group, a heterocycle, said alkyl, aryl, heteroaryl, heterocycle groups being optionally substituted;

R represents a hydrogen atom, an alkyl group, an aryl group, a heteroaryl group, a heterocycle, said alkyl, aryl, heteroaryl, heterocycle groups being optionally substituted;

m, m' and m" are integers chosen from 0 and 1;

q, q', q" are integers chosen from 0, 1, 2, 3, 4, 5, 6, 7, 8, 9 and 10;

n=1;

X represents a halogen atom, trifluoromethylsulfonate (triflate), methanesulfonate (mesylate), p-toluenesulfonic acid (tosylate).

In this embodiment, preferably:

$R^1$, $R^2$ and $R^3$ represent, independently of each other, a hydrogen atom, an alkyl group chosen from methyl, ethyl, propyl, butyl, pentyl, hexyl, heptyl groups, and the branched isomers thereof; aryl, optionally substituted, chosen from benzyl, phenyl, o-toluyl, m-toluyl, p-nitrophenyl, o-methoxyphenyl, m-methoxyphenyl and p-methoxyphenyl, o-methoxybenzyl, p-methoxybenzyl, m-methoxybenzyl, o-methylbenzyl, p-methylbenzyl and m-methylbenzyl;

R represents a hydrogen atom; an alkyl group chosen from methyl, ethyl, propyl, butyl, pentyl, hexyl, heptyl groups, and the branched isomers thereof; an aryl group, optionally substituted, chosen from o-methoxybenzyl, p-methoxybenzyl, m-methoxybenzyl, o-methylbenzyl, p-methylbenzyl and m-methylbenzyl. In this third embodiment, the method of the invention does not require the presence of a promoter. However, the use of an additive may be advantageous.

According to a fourth embodiment of the invention:

$R^1$ and $R^2$, taken together with the nitrogen atom to which they are bound, form a heterocycle, optionally substituted, and $R^3$ represents a hydrogen atom, an alkyl group, an aryl group, a heteroaryl group, a heterocycle, said alkyl, aryl, heteroaryl, heterocycle groups being optionally substituted;

R represents a hydrogen atom, an alkyl group, an aryl group, a heteroaryl group, a heterocycle, said alkyl, aryl, heteroaryl, heterocycle groups being optionally substituted;

m, m' and m" are integers chosen from 0 and 1;

q, q', q" are integers chosen from 0, 1, 2, 3, 4, 5, 6, 7, 8, 9 and 10;

n=1;

X represents a halogen atom, trifluoromethylsulfonate (triflate), methanesulfonate (mesylate) or p-toluenesulfonic acid (tosylate).

In this embodiment, preferably, $R^1$ and $R^2$, taken together with the nitrogen atom to which they are bound, form a heterocycle, optionally substituted, chosen from morpholine, piperidine, piperazine, pyrrolidine and tetrahydroisoquinoline, indoline and isoindoline, and $R^3$ represents a hydrogen atom; an alkyl group chosen from methyl, ethyl, propyl, butyl, pentyl, hexyl, heptyl groups, and the branched isomers thereof; an aryl group, optionally substituted, chosen from benzyl, phenyl, o-toluyl, m-toluyl, p-nitrophenyl, o-methoxyphenyl, m-methoxyphenyl and p-methoxyphenyl, o-methoxybenzyl, p-methoxybenzyl, m-methoxybenzyl, o-methylbenzyl, p-methylbenzyl and m-methylbenzyl;

R represents a hydrogen atom; an alkyl group chosen from methyl, ethyl, propyl, butyl, pentyl, hexyl, heptyl groups, an aryl group, optionally substituted, chosen from benzyl, o-methoxybenzyl, p-methoxybenzyl, m-methoxybenzyl, o-methylbenzyl, p-methylbenzyl and m-methylbenzyl, and the branched isomers thereof.

In this embodiment, preferably, X represents a halogen atom chosen from fluorine, chlorine, bromine and iodine.

In this fourth embodiment, the method of the invention does not require the presence of a promoter. However, the use of an additive may be advantageous.

In all the variants and all the embodiments of the invention, the values of m, m', m", q, q' and q" in the alkylamines of formula (I) are preferably chosen so that:

0≤m+q≤10; and/or
0≤m'+q'≤10; and/or
0≤m"+q"≥10.

In all the variants and all the embodiments of the invention, the reducing agent is, in particular, chosen from $H_2$, a silane of formula (III)

and
a borane of formula (IV)

wherein $R^4$, $R^5$, $R^6$, $R^7$ and $R^8$ represent, independently of each other, a hydrogen atom, an alkyl group, an alkoxy group, an alkenyl group, an alkynyl group, an aryl group, a heteroaryl group, a heterocycle, a silyl group, a siloxy group, an amino group, said alkyl, alkenyl, alkynyl, aryl, heteroaryl, heterocycle, silyl, siloxy and amino groups being optionally substituted; or $R^7$ and $R^8$ taken together with the boron atom to which they are bound, form a heterocycle, optionally substituted.

More particularly, the reducing agent is chosen from $H_2$, a silane of formula (III) and a borane of formula (IV), wherein $R^4$, $R^5$, $R^6$, $R^7$ and $R^8$ represent, independently of each other, a hydrogen atom; an alkyl group chosen, for example, from methyl, ethyl, propyl, butyl, pentyl, hexyl, heptyl groups and the branched isomers thereof; cyclohexyl; an alkoxy group chosen, for example, from methoxy and ethoxy; an aryl group, optionally substituted, chosen for example from benzyl and phenyl; a siloxy group chosen for example from trimethylsiloxy —OSi(CH$_3$)$_3$, triethylsiloxy —OSi(CH$_2$CH$_3$)$_3$, tert-butyldiphenylsiloxy —OSi(tBuPh$_2$)$_3$, methylsiloxy (—OSi(H)$_2$(CH$_3$), dimethylsiloxy (—OSi(H)(CH$_3$)$_2$), ethylsiloxy (—OSi(H)$_2$(C$_2$H$_5$), diethylsiloxy (—OSi(H)(C$_2$H$_5$)$_2$), tetramethyldisiloxane (TMDS or O(Si(Me)$_2$H)$_2$) and polymethylhydrosiloxane (PMHS);

$R^7$ and $R^8$ taken together with the boron atom to which they are bound, form a heterocycle, said heterocycle being chosen from catecholborane (catBH), pinacolborane (pinBH) or 9-borabicyclo[3.3.1]nonane (9-BBN).

Even more particularly, the reducing agent is chosen from H$_2$ and a silane of formula (III) wherein R$^4$, R$^5$, R$^6$, R$^7$ and R$^8$ represent, independently of each other, a hydrogen atom; an alkyl group chosen, for example, from methyl, ethyl, propyl, butyl, pentyl, hexyl, heptyl groups and the branched isomers thereof; cyclohexyl; an alkoxy group chosen, for example, from methoxy and ethoxy; an aryl group, optionally substituted, chosen for example from benzyl and phenyl; a siloxy group chosen for example from dimethylsiloxy (—OSi(H)(CH$_3$)$_2$), ethylsiloxy (—OSi(H)$_2$(C$_2$H$_5$), and polymethylhydrosiloxane (PMHS);

By way of example of reducing agent, mention can be made of H$_2$, (C$_6$H$_5$)SiH$_3$, (C$_6$H$_5$)$_2$SiH$_2$, (CH$_3$CH$_2$)$_3$SiH, (EtO)$_3$SiH, dimethylsiloxane, polymethylhydrosiloxane (PMHS), tetramethyldisiloxane (TMDS or O(Si(Me)$_2$H)$_2$).

As already mentioned, the presence of a promoter may be advantageous in the first and second embodiments where n=0.

The promoter may be of formula RX, with R representing a hydrogen atom, an alkyl group, a heteroaryl group, an aryl group, a heterocycle, said alkyl, aryl, heteroaryl, heterocycle groups being optionally substituted; and X representing a halogen atom, trifluoromethylsulfonate (triflate), methanesulfonate (mesylate), p-toluenesulfonic acid (tosylate).

The promoter may also be a quaternary ammonium salt of formula R$_9$R$_{10}$R$_{11}$R$_{12}$NX wherein R$_9$, R$_{10}$, R$_{11}$, R$_{12}$ represent, independently of each other, a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted, with the alkyl, alkenyl, alkynyl, aryl, heteroaryl, heterocycle groups as defined in the context of the present invention; and X represents a halogen atom chosen from fluorine, chlorine, bromine and iodine atoms; trifluoromethylsulfonate (triflate), methanesulfonate (mesylate) and p-toluenesulfonic acid (tosylate).

The promoter is advantageously of formula RX.

More advantageously, the promoter is of formula RX with R representing an alkyl group chosen from methyl, ethyl, propyl, butyl, pentyl, hexyl, heptyl groups, and the branched isomers thereof; an aryl group, optionally substituted, chosen from benzyl, o-methoxybenzyl, p-methoxybenzyl, m-methoxybenzyl, o-methylbenzyl, p-methylbenzyl and m-methylbenzyl; and X representing a halogen atom chosen from fluorine, chlorine, bromine and iodine.

By way of example of promoter, mention can be made of iodomethane, iodoethane, iodopropane and iodobutane.

In all the variants and all the embodiments of the invention, the catalyst may be a metal catalyst chosen from metal salts and complexes.

The metal may then be a transition metal chosen from chromium, tungsten, manganese, rhenium, silver, ruthenium, rhodium, cobalt, iron, nickel, copper, iridium, osmium, molybdenum, gold, platinum and palladium.

When the metal catalyst is a metal salt, the anions able to form salts with the aforementioned transition metals are chlorine (Cl$^-$), sulphate (SO$_4^{2-}$), sulphur (S$^{2-}$), nitrate (NO$_3^-$), oxide (O$^{2-}$) and hydroxide (OH$^-$). In this regard, mention can be made for example of CuCl, PtCl$_2$, PdCl$_2$, MnSO$_4$, COCl$_2$, FeCl$_2$ and FeCl$_3$.

The catalyst may also be a metal complex.

Metal complex means an organometallic or inorganic coordination compound in which a metal ion is bound to an organic or inorganic ligand. An organometallic or inorganic complex can be obtained by mixing a metal salt with a ligand, the latter binding to the metal via phosphorus, carbon, nitrogen, oxygen, hydrogen or silicon atoms, for example.

When the metal catalyst is a metal complex, the ligands that can be bound to the aforementioned transition metals can be chosen from:

nitrogenous bases such as for example secondary or tertiary amines chosen from trimethylamine, triethylamine, piperidine, 4-dimethylaminopyridine (DMAP), 1,4-diazabicyclo[2.2.2]octane (DABCO), proline, phenylalanine, a thiazolium salt, N-diisopropylethylamine (DIPEA or DIEA), bipyridyl (bipy), terpyridine (terpy); phenanthroline (phen), ethylenediamine, N,N,N',N'-tetra-methyl-ethylenediamine (TMEDA), quinoline and pyridine;

phosphorous bases such as for example alkyl and aryl phosphines chosen from triphenylphosphine, 2,2'-bis(diphenylphosphino)-1,1'-binaphthyl (BINAP), triisopropylphosphine, tris[2-diphenylphosphino)ethyl] phosphine (PP$_3$), tricyclohexylphosphine, 1,2-bis-diphenylphosphinoethane (dppe), 1,2-bis (diphenylphosphino)ethane (dppb); alkyl and aryl phosphonates chosen from diphenylphosphate, triphenylphosphate (TPP), tri(isopropylphenyl)phosphate (TIPP), cresyldiphenyl phosphate (CDP), tricresylphosphate (TCP); alkyl and aryl phosphates chosen from di-n-butylphosphate (DBP), tris-(2-ethylhexyl)-phosphate and triethyl phosphate;

oxygenated bases such as for example acetate (OAc), acetylacetonate, methanolate, ethanolate, benzoyl peroxide;

silylated ligands such as for example alkylsilyls or arylsilyles chosen from triphenylsilyl, diphenylhydrosilyl, trimethylsilyl, dimethylhydrosilyl, triethylsilyl, triethoxysilyl;

carbonaceous ligands chosen from for example CO, CN—, and the N-heterocyclic carbenes from an imidazolium salt chosen from the salts of 1,3-bis(2,6-diisopropylphenyl)-1H-imidazol-3-ium (IPr), 1,3-bis (2,6-diisopropylphenyl)-4,5-dihydro-1H-imidazol-3-ium, 1,3-bis(2,4,6-trimethylphenyl)-1H-imidazol-3-ium (IMes), 1,3-bis(2,4,6-trimethylphenyl)-4,5-dihydro-1H-imidazol-3-ium, 4,5-dichloro-1,3-bis(2,6-diisopropylphenyl)-1H-imidazol-3-ium, 1,3-di-tert-butyl-1H-imidazol-3-ium (also referred to a "ItBu" or "ItBu carbene"), 1,3-di-tert-butyl-4,5-dihydro-1H-imidazol-3-ium, said salts being in the form of chloride salts.

Examples of N-heterocyclic carbenes are represented below:

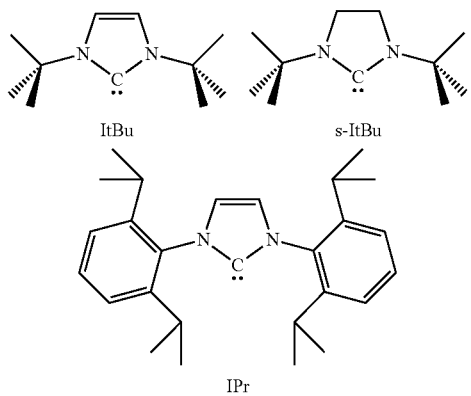

ItBu s-ItBu

IPr

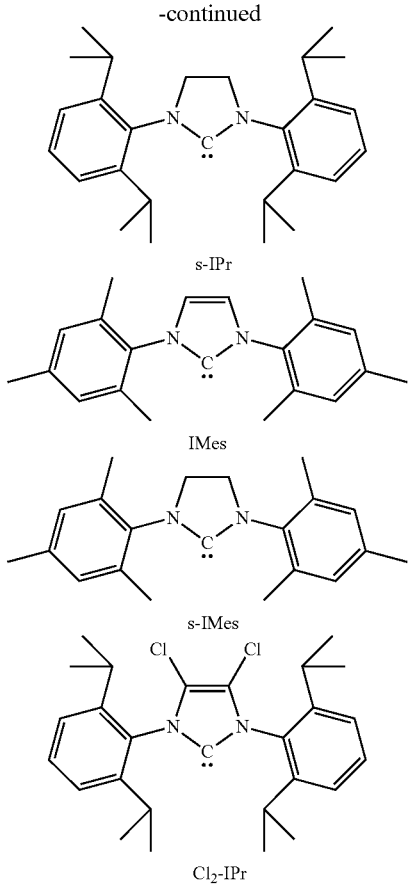

s-IPr

IMes s-IMes

Cl₂-IPr

The metal complex may optionally comprise a counterion chosen from for example sodium (Na+), potassium (K+) and ammonium (NH₄+).

The metal complex may be bimetallic. In bimetal complexes, some ligands may be "bridged", that is to say bound simultaneously to two metal centres, such as for example CO₂CO, Fe₂CO₉ or Fe₃CO₁₂.

By way of example of metal complexes, mention can be made of CO₂CO₈, [Fe(CO)₅], [Ir(CO)(Cl)(PPh₃)₂], [Cr(CO)₃(η⁶-C₆H₆)], Fe(acac)₃, Cu(OAc)₂(H₂O), NaCoCO₄, MoCO₆, FeCO₅ and CO₂CO₈ optionally in the presence of bipyridyl (bipy), terpyridine (terpy) or phenanthroline (phen).

Preferably, the ligands used are
carbonaceous ligands chosen from for example CO, CN–, 1,3-bis(2,4,6-trimethylphenyl)-1H-imidazol-3-ium (IMes) and 1,3-bis(2,6-diisopropylphenyl)-1H-imidazol-3-ium (IPr);
nitrogenous bases such as for example secondary or tertiary amines chosen from bipyridyl (bipy), phenanthroline (phen), terpyridine (terpy), quinoline.

Preferably, the metal is chosen from cobalt, iron and molybdenum.

The metal complexes preferentially used are NaCoCO₄, MoCO₆, FeCO₅, Fe₃CO₁₂ and CO₂CO₈ optionally in the presence of bipyridyl (bipy), terpyridine (terpy) or phenanthroline (phen) in order to form [(bipy)₃Co]²⁺ ([CoCO4]⁻)₂, [(terpy)₂Co]²⁺[CoCO4]⁻, [(phen)₃Co]²⁺ [CoCO4]⁻.

In all the variants and all the embodiments of the invention, the catalyst is preferably a metal complex.

Some of the abbreviations used for the ligands are represented below:

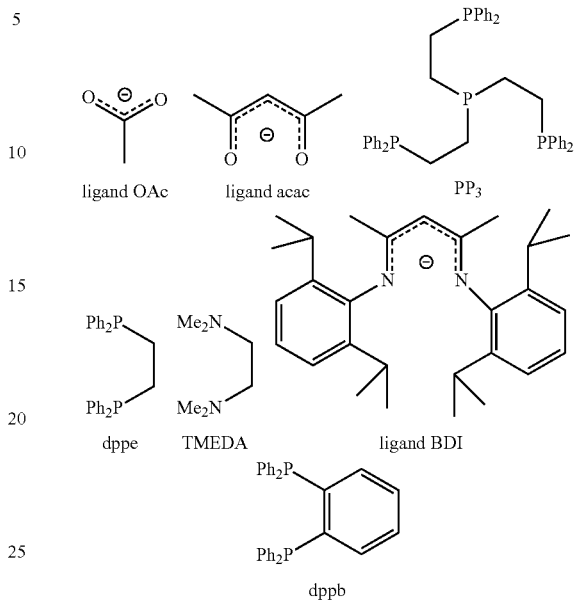

ligand OAc   ligand acac   PP₃ dppe   TMEDA   ligand BDI dppb

The catalysts may, where necessary, be immobilised on heterogeneous supports, for example in order to ensure easy separation of said catalyst and/or recycling thereof. Said heterogeneous supports may be chosen from supports based on silica gel or plastic polymers such as for example polystyrene; carbonaceous supports chosen from carbon nanotubes; silicon carbide; alumina; or magnesium chloride (MgCl₂).

The method of the invention may further be conducted in the presence of an additive. The additives may be chosen from amides, in particular aromatic, such as for example acetanilide, benzanilide and N-methylacetanilide; Lewis acids such as for example AlCl₃, LiCl, LiBF₄, FeCl₃, InCl₃, BiCl₃.

In the method according to the invention, the reaction may occur under CO pressure. The pressure of the CO may then be between 1 and 200 bar, preferably between 1 and 100 bar, more preferably between 1 and 60 bar, inclusively.

A mixture of CO and H₂ may also be used. In this case, the H₂ pressure is independent of that of CO. The CO pressure may then be between 1 and 200 bar, preferably between 1 and 100, more preferentially between 1 and 60 bar, inclusively, and the H₂ pressure may be between 1 and 100 bar, preferably between 1 and 50 bar, and more preferentially between 5 and 30 bar, inclusively.

In the presence of silane of formula (III) or borane of formula (IV) as a reducing agent, a CO pressure is preferred to a mixture of CO and H₂ pressures.

The reaction may be conducted at a temperature of between 25 and 300° C., preferably between 50 and 250° C., more preferably between 80 and 200° C., inclusively.

The reaction time depends on the degree of conversion of the amine of formula (II). Thus, the optimum reaction time corresponds to the complete conversion of the amine of formula (II). The reaction time is between 1 hour and 72 hours, advantageously preferably between 3 and 24 hours, inclusively.

The method of the invention, in particular the reaction between the various reagents, may be conducted in a solvent or a mixture of at least two solvents chosen from:
- ethers chosen from diethyl ether, THF, dioxane and diglyme;
- amides chosen from N-methyl-2-pyrrolidone (NMP) and N,N-dimethylformamide (DMF);
- hydrocarbons chosen from benzene, toluene, pentane and hexane;
- nitrogenous solvents chosen from pyridine and acetonitrile;
- water;
- sulfoxides such as dimethylsulfoxide;
- alkyl halides chosen from chloroform and methylene chloride;
- aryl halides chosen from chlorobenzene and dichlorobenzene.

The concentration of the amine of formula (II) in the reaction medium is between 0.01 and 10 M, preferably between 0.1 and 5 M, more preferably between 0.1 and 2 M, inclusively.

The amount of catalyst is from 0.00001 to 1 molar equivalent, preferably 0.0001 to 0.9 molar equivalent, more preferably from 0.0001 to 0.2 molar equivalent, even more preferably from 0.001 to 0.1 molar equivalent, inclusively, with respect to the amine of formula (II).

When the method uses a promoter, the amount of promoter is between 0.00001 and 1 molar equivalent, preferably between 0.01 and 0.9 molar equivalent, more preferably between 0.1 and 0.4 molar equivalent, inclusively, with respect to the amine of formula (II).

When the method uses an additive, the amount of additive is between 0.00001 and 0.5 molar equivalent, preferably between 0.01 and 0.9 molar equivalent, more preferably between 0.1 and 0.4 molar equivalent, inclusively, with respect to the amine of formula (II).

The various reagents used in the method of the invention, the amines of formula (II), the reducing agents, the catalysts, the promoters, the additives, etc. are, in general, commercially available compounds or compounds that can be prepared by methods known to persons skilled in the art.

The method of the invention makes it possible to prepare also marked alkylamines of formula (I). This constitutes another subject matter of the invention. Marked alkylamines correspond to alkylamines of formula (I) comprising at least one radiomarker/radiotracer or a chosen isotope.

"Isotopes" means, for a same element, two atoms having the same number of protons (and electrons) but a different number of neutrons. Having the same number of electrons and protons, the chemical properties of the isotopes of the same element are almost identical. There may however exist slight variations in the speed of a chemical reaction when one of the atoms of a reagent is replaced by one of its isotopes. On the other hand, as the nucleus does not comprise the same number of neutrons, the mass of the atoms varies, which may render the atom unstable: this is why they may be radioactive. These are then radioisotopes. In the context of the invention, the term "isotopes" may also encompass the "radioisotopes".

Radiomarking is the fact of associating, with a given molecule or compound, an isotope that will allow to monitor the development and/or the fixing of the molecules, for example in an organ. The radiotracer is the radioactive element or elements present in a molecule for monitoring the path of this substance, for example in an organ.

The present method may thus give access to the $^{11}C$, $^{13}C$, $^{14}C$ $^{15}N$, $^{17}O$, $^{18}O$, $^{18}F$, $^{29}Si$, $^{30}Si$, $^{33}S$, $^{34}S$, $^{36}S$, $^{2}H$ (D) and/or $^{3}H$ (T) marked alkylamines.

The temperature, reaction time and solvent conditions, as well as the amounts of reagents and catalysts used in the method for preparing marked alkylamines, are those described above in the context of the method for preparing alkylamines of formula (I).

The use of molecules for the purpose of tracing, metabolisation, imaging, etc. is detailed in the literature (U. Pleiss, R. Voges, "Synthesis and Applications of Isotopically Labelled Compounds, Volume 7", Wiley-VCH, 2001; R. Voges, J. R. Heys, T. Moenius, "Preparation of Compounds Labelled with Tritium and Carbon-14". Wiley-VCH: Chippenham (UK), 2009). The possibility of forming the marked alkylamines may be provided by the availability of the corresponding marked reagents, for example:
- $R^1R^2NH$ amines enriched with $^{15}N$ are accessible from $^{15}N$ enriched ammonium chloride: [$^{15}NH_4$][Cl] (Yong-Joo Kim, Max P. Bernstein, Angela S. Galiano Roth, Floyd E. Romesberg, Paul G. Williard, David J. Fuller, Aidan T. Harrison and David B. Collum, *J. Org. Chem.* 1991, 56, p. 4435-4439);
- $R^1R^2NH$ amines with marked $R^1$ and/or $R^2$ marked are prepared by the synthesis methods detailed by U. Pleiss, R. Voges, "Synthesis and Applications of Isotopically Labelled Compounds", Volume 7, Wiley-VCH, 2001; and R. Voges, J. R. Heys, T. Moenius, "Preparation of Compounds Labelled with Tritium and Carbon-14", Wiley-VCH: Chippenham (UK), 2009);
- $^{11}C$ or $^{14}C$ marked CO is the main source of $^{11}C$ and $^{14}C$ and is obtained by solidification of $Ba^{14}CO_3$ marked barium (R. Voges, J. R. Heys, T. Moenius, "Preparation of Compounds Labelled with Tritium and Carbon-14", Wiley-VCH: Chippenham (UK), 2009);
- iodoalkanes such as for example $^{13}CH_3I$, $^{13}CH_3^{13}CH_2I$ and $^{14}CH_3I$ are respectively commercially available and easily synthesisable from $Ba^{14}CO_3$ (R. Voges, J. R. Heys, T. Moenius, "Preparation of Compounds Labelled with Tritium and Carbon-14", Wiley-VCH: Chippenham (UK), 2009).

Preferably, $^{11}C$, $^{14}C$ or $^{13}C$ marked CO is used in the method for preparing marked alkylamines of formula (I').

$^{14}C$ marked molecules have contributed to many advances in life sciences (enzymatic mechanisms, biosynthesis mechanisms, biochemistry), environmental sciences (tracing of waste), research (elucidation of reaction mechanisms) or also in diagnostics and research and development in novel pharmaceutical and therapeutic products. $^{14}C$ marked molecules in fact have an advantage in metabolic studies since $^{14}C$ is easily detectable and quantifiable in both an in vitro environment and an in vivo environment.

The main source of $^{14}C$ is $^{14}CO$, which is obtained by acidification of barium carbonate $Ba^{14}CO_3$. The development of methods for the synthesis of base molecules used for producing drugs is essential in producing $^{14}C$ marked active ingredients whose metabolism can thus be determined (R. Voges, J. R. Heys, T. Moenius, "Preparation of Compounds Labelled with Tritium and Carbon-14", Wiley-VCH: Chippenham (UK), 2009).

The major constraint limiting the synthesis of $^{14}C$ marked molecules is the need to have a high yield of $^{14}C$ product formed with respect to the amount of $^{14}CO$ used and to be based on a small number of steps in order to minimize the costs related to the use of $Ba^{14}CO_3$ (U. Pleiss, R. Voges, "Synthesis and Applications of Isotopically Labelled Compounds, Volume 7", Wiley-VCH, 2001; R. Voges, J. R. Heys, T. Moenius, "Preparation of Compounds Labelled with Tritium and Carbon-14", Wiley-VCH: Chippenham (UK) 2009).

Another subject matter of the invention is the use of the method for preparing alkylamines of formula (I) according to the invention, in the manufacturing of vitamins, pharmaceutical products, adhesives, acrylic fibres and synthetic leathers, pesticides, surfactants, detergents and fertilisers.

Another subject matter of the invention is the use of the method for preparing marked alkylamines of formula (I) according to the invention, in the manufacturing of radiotracers and radiomarkers. By way of examples of radiotracers and radiomarkers, mention can be made of 6-bromo-7-[$^{11}$C]methylpurine and 6-bromo-7-[$^{14}$C]methylpurine, [N-[$^{14}$C]methyl]-2-(4'-(methylamino) phenyl)-6-hydroxybenzothiazole (also known as [$^{14}$C]PIB), whose structures are represented below:

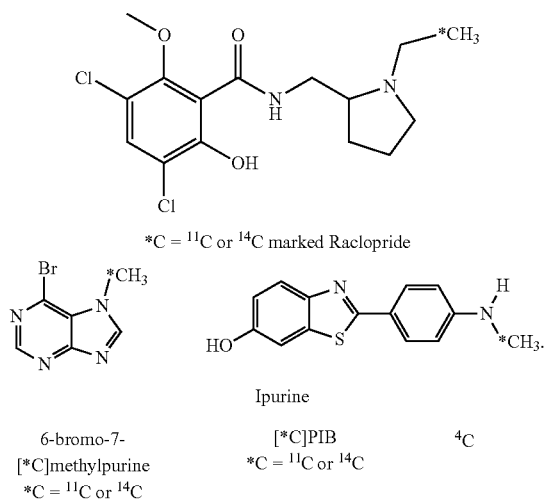

Another subject matter of the invention is a method for manufacturing vitamins, pharmaceutical products, adhesives, acrylic fibres, synthetic leathers, pesticides, fertilisers, surfactants, detergents characterised in that it comprises (i) a step of preparing alkylamines of formula (I) by the method according to the invention, and optionally (ii) a hydrolysis step or an acidification step, in order to form for example the corresponding chlorohydrate, borohydrate, fluorohydrate or iodohydrate. At the end of the hydrolysis, optionally a distillation or a concentration under vacuum may be necessary.

Another subject matter of the invention is a method for manufacturing tracers and radiotracers, characterised in that it comprises (i) a step of preparing marked alkylamines of formula (I) by the method according to the invention, and optionally (ii) a hydrolysis step or an acidification step in order to form for example the corresponding chlorohydrate, borohydrate, fluorohydrate or iodohydrate. At the end of the hydrolysis, optionally a distillation or a concentration under vacuum may be necessary.

As already mentioned, the method according to the invention leads to the formation of alkylamines, wherein the length of the alkyl chains present may be different. In other words, the method of the invention makes it possible to create and/or lengthen the alkyl chain or chains present on the amines of formula (II), in an independent and controlled manner.

Any by-products formed during the method of the invention correspond in general to the amides resulting from the carbonylation of the corresponding alkylamines formed. By a simple filtration it is possible to recover the catalyst, optionally supported, and to eliminate some of the by-products optionally formed. The amides may be separated by filtration on silica, recycled and re-used in the method of the invention.

By acting on the operating conditions, as shown in the examples, the formation of the by-products and the extension of the alkyl chain and/or chains can be controlled.

Other advantages and features of the present invention will become apparent upon reading the following examples given by way of illustration and as limitations, and with reference to the accompanying figures.

Figure 1:
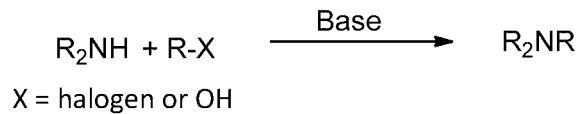
FIG. 1 shows the alkylation of amines using alcohols or haloalkanes via the Fischer-Tropsch method.
Figure 2:
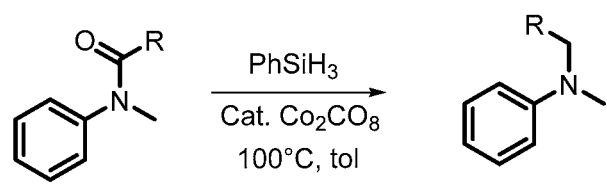
FIG. 2 shows the reduction of amides into amines by hydrosilylation of the amides in the presence of $Co_2CO_8$ as a catalyst.
Figure 3:
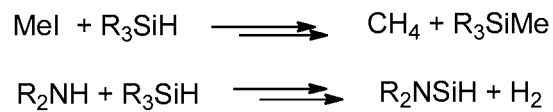

FIG. 3 shows the undesirable reactions likely to occur when the carbonylation reaction is conducted in the presence of a reducing agent and a promoter and when the reduction is conducted in the presence of CO. For example, the silanes (reducing agent) are known to form methane in the presence of iodomethane (promoter), which would deactivate the system, or to form a silylated amine in the presence of an amine.

EXAMPLES

In all the examples, the reagents used, in particular the amine of formula (II), the catalyst, the promoter and the reducing agent are commercially available products or can be synthesised by following the procedures described in the literature. In particular the synthesis of $NaCoCO_4$ is described in F. W. Edgell, J. Lyford, *Inorg. Chem.*, 1970, 1932, and the synthesis of N-methyl-1,2,3,4-tetrahydroisoquinoline in C. Casagrande, A. Galli, R. Ferrini, G. Miragoli, *Farmaco, Edizione Scientifica*, 1972, 445. The remainder of the products used are purchased from Sigma-Aldrich.

Example 1: Preparation of Alkylamines of Formula (I) with Variable Chain Lengths The method for preparing alkylamines of formula (I) can be implemented in a single step and in a single reaction mixture and in the same autoclave (one step one-pot) according to the following experimental protocol.

An autoclave is loaded in a glovebox with the catalyst (between 0.001 and 0.1 molar equivalent), the amine of formula (II) (1 molar equivalent), the promoter (between 0.1 and 1 molar equivalent), the reducing agent (between 1 and 6 molar equivalents), optionally an additive and the solvent. The concentration of amine of formula (II) in the reaction medium is between 0.05 M and 0.3 M. The introduction order is not of importance.

The autoclave is sealed and then purged several times (4 times) with 10 bar of CO and then the temperature is raised to between 50 and 200° C. in 35 minutes. The CO pressure is maintained between 1 and 100 bar. The reaction time is from 1 to 24 hours.

Once the reaction has ended, the autoclave is cooled to ambient temperature (20±5° C.). The crude reaction mixture is filtered on Celite. The volatile compounds are eliminated under reduced pressure and the reaction mixture containing the various alkylamines is purified by silica gel chromatography using a mixture of ethyl acetate and n-pentane as eluent for obtaining analytically pure alkylamines.

A set of results is presented below in Table 1, giving examples of conversions of amines of formula (II) into alkylamines (determined by NMR) using phenylsilane PhSiH$_3$ (sold by Aldrich) as a reducing agent, optionally CH$_3$I (sold by Aldrich) as a promoter, and Co$_2$CO$_8$ and FeCO$_5$ (sold by Aldrich) as catalysts, in accordance with the conditions presented below.

TABLE 1

| Amine | Reducing agent | Catalyst | Conditions | Conversion | Products |
|---|---|---|---|---|---|
| 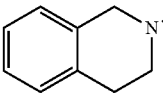 | PhSiH$_3$ (2 eq.) | Co$_2$CO$_8$ (0.06 eq.) | CO 60 bar, 7 h, 200° C. Promoter: CH$_3$I (0.33 eq.) Solvent: MeCN (0.3M) | 88% | 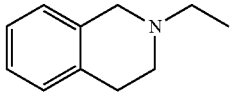 20% 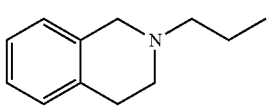 8% 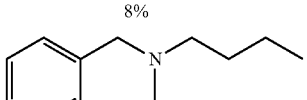 3% 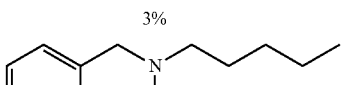 2% |
| 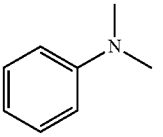 | PhSiH$_3$ (2 eq.) | FeCO$_5$ (0.06 eq.) | CO 60 bar, 7 h, 200° C. Promoter: CH$_3$I (0.33 eq.) Solvent: MeCN (0.3M) | 65% | 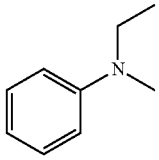 25% 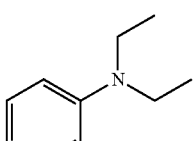 5% |
| 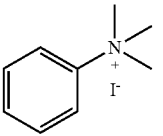 | PhSiH$_3$ (1.5 eq.) | Co$_2$CO$_8$ (0.06 eq.) | CO 50 bar, 10 h, 200° C. Solvent: MeCN (0.2M) | 93% | 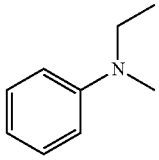 3% 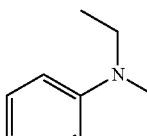 16% |

TABLE 1-continued

| Amine | Reducing agent | Catalyst | Conditions | Conversion Products |
|---|---|---|---|---|
| PhN(CH₃)₃⁺ I⁻ (N,N,N-trimethylanilinium iodide) | PhSiH₃ (1.5 eq.) | Co₂CO₈ (0.06 eq.) | CO 50 bar, 7 h, 180° C. Solvent: MeCN (0.2M) | 78% PhN(Et)(Me) 56%; PhNEt₂ 12% |

The yields are determined by GC/MS. The alkylamine yields have not been optimised but are encouraging. The by-products obtained are the corresponding amides. They can be recycled and can serve as starting products.

The results show that the operating conditions specified above lead to mixtures of alkylamines wherein the length of each alkyl chain may be different and vary independently. The reaction conditions are therefore very important for the selectivity and efficacy of the reaction.

Example 2: Preparation of Alkylamines of Formula (I) with Variable Chain Lengths The same operating method as the one in example 1 is followed. In this example, various reducing agents were tested.

The results are presented below in Table 2.

TABLE 2

| Amine | Reducing agent | Catalyst | Conditions | Conversion Products |
|---|---|---|---|---|
| PhN(CH₃)₃⁺ I⁻ (0.2M) | PhSiH₃ (2 eq.) | Co₂CO₈ (0.06 eq.) | CO 50 bar, 7 h, 200° C., Solvent: MeCN (0.2M) | 99% PhN(Et)(Me) 10%; PhNEt₂ 16% |

TABLE 2-continued

| Amine | Reducing agent | Catalyst | Conditions | Conversion | Products |
|---|---|---|---|---|---|
| PhN(Me)₂Me⁺ I⁻ (0.2M) | PhSiH₃ (3 eq.) | Co₂CO₈ (0.06 eq.) | CO 50 bar, 7 h, 200° C. Solvent: MeCN (0.2M) | 90% | PhN(Me)(Et) 18%; PhN(Et)₂ 9% |
| PhN(Me)₂Me⁺ I⁻ (0.2M) | Ph₂SiH₂ (2 eq.) | Co₂CO₈ (0.06 eq.) | CO 50 bar, 7 h, 200° C. Solvent: MeCN (0.2M) | 99% | PhN(Me)(Et) 6% |
| PhN(Me)₂Me⁺ I⁻ (0.2M) | H₂ (50 bar) | Co₂CO₈ (0.06 eq.) | CO 50 bar, 15 h, 200° C. Solvent: MeCN (0.2M) | 40% | PhN(Me)(Et) 2%; PhN(Et)(Me) 2% |
| PhN(Me)₂Me⁺ I⁻ (0.2M) | Et₃SiH (2 eq.) | Co₂CO₈ (0.06 eq.) | CO 50 bar, 15 h, 200° C. Solvent: MeCN (0.2M) | 94% | PhN(Me)(Et) 4% |

The amount of reducing agent and the type of reducing agent are crucial factors since the yield depends on this significantly. The yields are determined by GC/MS. The alkylamine yields were not optimised but are encouraging. The by-products obtained are the corresponding amides that come from the carbonylation of the corresponding alkylamines. These amides can be recycled and can serve as starting products.

Example 3: Preparation of Alkylamines of Formula (I) with Controlled Chain Lengths A) Control by Reaction in Two Steps in the Same Autoclave (Two Steps One-Pot)

The method for preparing alkylamines of formula (I) can be implemented in two steps and in a single reaction mixture (two steps one-pot) according to the following experimental protocol.

An autoclave is loaded in a glovebox with the catalyst (between 0.001 and 0.1 molar equivalent), the amine of formula (II) (1 equivalent), the promoter (between 0.3 and 1 molar equivalent) and the solvent. The concentration of amine of formula (II) in the reaction medium is between 0.01 M and 0.3 M. The introduction order is of no importance.

The autoclave is sealed and then purged several times (4 times) with 10 bar of CO and then the temperature is raised to between 150 and 200° C. in 35 minutes. The CO pressure is maintained between 1 and 100 bar. The reaction time is 1 to 24 hours.

The autoclave is next purged 4 times with 5 bar of argon and then the reducing agent (between 1 and 6 molar equivalents) is introduced. The autoclave is next heated to between 50 and 200° C. for 1 to 10 hours.

Once the reaction has ended, the autoclave is cooled to ambient temperature (20±5° C.). The crude reaction mixture is filtered on Celite. The volatile compounds are eliminated under reduced pressure and the reaction mixture containing the various alkylamines is purified by silica gel chromatography using a mixture of ethyl acetate/n-pentane as eluent to obtain analytically pure alkylamines.

The reaction scheme is as follows:

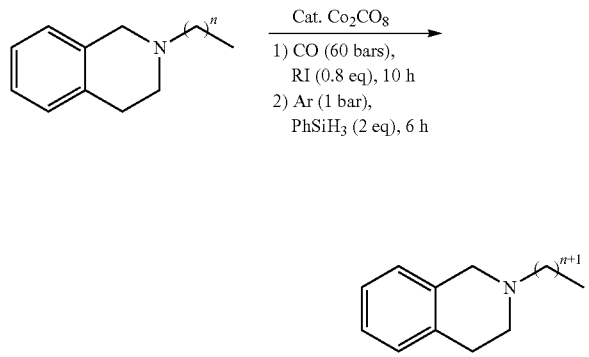

This result shows that the operating conditions specified above lead to an alkylamine whose alkyl chain is lengthen in a controlled manner. All the converted amine gives the corresponding alkylamine. The reaction is therefore particularly clean since no by-product is obtained. In addition, the amine that has not reacted can be recycled.

B) Control by Pressure

A Wilmad NMR tube (or an autoclave) is loaded in a glovebox with the catalyst (between 0.001 and 0.1 molar equivalent), the amine of formula (II) (1 equivalent), the promoter (between 0.3 and 1 molar equivalent) and the solvent. The concentration of amine is between 0.01 M and 0.3 M. The introduction order is of no importance.

An additive (between 0.05 and 1 molar equivalent) may be added in order to promote the reaction. This additive may be an amide or a Lewis acid as described previously.

The tube is sealed and then purged a plurality of times (twice) with 10 bar of CO. The tube is next pressurised at a CO pressure of between 1 and 30 bar. The tube is next heated to between 50° C. and 150° C.

Once the reaction has ended, the autoclave is cooled to ambient temperature (20±5° C.). The crude reaction mixture is filtered on Celite. The volatile compounds are eliminated under reduced pressure and the reaction mixture containing the alkylamines is purified by silica gel chromatography using a mixture of ethyl acetate and n-pentane as eluent in order to obtain the analytically pure alkylamines.

A set of results is presented below in Table 4, giving examples of conversions of amines of formula (II) into alkylamines (determined by NMR) using phenylsilane $PhSiH_3$ (sold by Aldrich) as a reducing agent, optionally $CH_3I$ and $CH_3CH_2I$ (sold by Aldrich), as a promoter, N-ethylacetanilide and $AlCl_3$ as additives (sold by Aldrich), and $Co_2CO_8$, and $Co_2CO_8$+bpy and $FeCO_5$ (sold by Aldrich), and $NaCoCO_4$ manufactured according to the method described in the reference mentioned above, as catalysts, according to the conditions presented below.

TABLE 3

| Amine | Reducing agent | Catalyst | Conditions | Conversion | Products |
|---|---|---|---|---|---|
| [tetrahydroisoquinoline-N-CH₃] | $PhSiH_3$ (2 eq.) | $Co_2CO_8$ (0.06 eq.) | 1) CO 60 bar, catalyst, promoter ($CH_3I$ 0.8 eq.), 200° C., 10 h 2) Ar 1 bar, reducing agent, 200° C., 6 h | 70% | [tetrahydroisoquinoline-N-CH₂CH₃] 70% |

TABLE 4

| Amine | Reducing agent | Catalyst | Conditions | Conversion | Products |
|---|---|---|---|---|---|
| 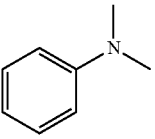 (0.3M) | PhSiH$_3$ (2 eq.) | Co$_2$CO$_8$ + bpy (0.06 eq.) | CO 8 bar, 17 h, 200° C. Promoter: CH$_3$I (0.3 eq.) Solvent: MeCN (0.3M) | 20% | 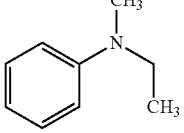 20% |
| 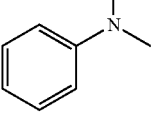 (0.3M) | PhSiH$_3$ (2 eq.) | Co$_2$CO$_8$ + bpy (0.06 eq.) | CO 8 bar, 17 h, 200° C. Promoter: CH$_3$I (0.3 eq.) Additive: N-ethyl-acetanilide (0.3 eq.) Solvent: MeCN (0.3M) | 50% | 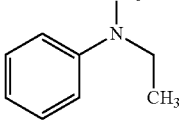 50% |
| 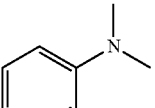 (0.3M) | PhSiH$_3$ (2 eq.) | Co$_2$CO$_8$ (0.06 eq.) | CO 8 bar, 17 h, 200° C. Promoter: CH$_3$I (0.3 eq.) Additive: N-ethyl-acetanilide (0.3 eq.) Solvent: MeCN (0.3M) | 46% | 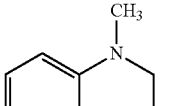 46% |
| 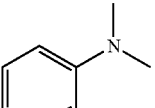 (0.3M) | PhSiH$_3$ (2 eq.) | NaCoCO$_4$ (0.06 eq.) | CO 8 bar, 17 h, 200° C. Promoter: CH$_3$I (0.3 eq.) Additive: N-ethyl-acetanilide (0.3 eq.) Solvent: MeCN (0.3M) | 46% | 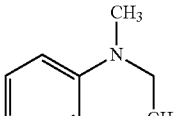 46% |
| 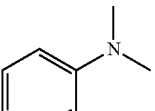 (0.3M) | PhSiH$_3$ (2 eq.) | Co$_2$CO$_8$ (0.06 eq.) | CO 8 bar, 17 h, 200° C. Promoter: CH$_3$I (0.3 eq.) Additive: N-ethyl-acetanilide (0.3 eq.) Solvent: toluene (0.3M) | 25% | 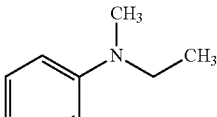 25% |
| 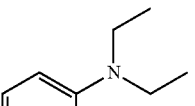 (0.3M) | PhSiH$_3$ (2 eq.) | Co$_2$CO$_8$ (0.06 eq.) | CO 8 bar, 17 h, 200° C. Promoter: CH$_3$CH$_2$I (0.3 eq.) Additive: N-ethyl-acetanilide (0.3 eq.) Solvent: MeCN (0.3M) | 17% | 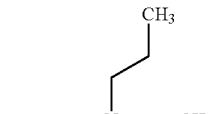 17% |
| 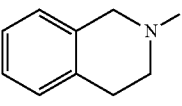 (0.3M) | PhSiH$_3$ (2 eq.) | Co$_2$CO$_8$ (0.06 eq.) | CO 8 bar, 17 h, 200° C. Promoter: CH$_3$I (0.3 eq.) Additive: N-ethyl-acetanilide (0.3 eq.) Solvent: toluene (0.3M) | 50% | 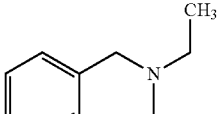 50% |

TABLE 4-continued

| Amine | Reducing agent | Catalyst | Conditions | Conversion | Products |
|---|---|---|---|---|---|
| PhN⁺(CH₃)₃ I⁻ (0.3M) | PhSiH₃ (2 eq.) | Co₂CO₈ (0.06 eq.) | CO 8 bar, 17 h, 200° C. Additive: N-ethyl-acetanilide (0.3 eq.) Solvent: MeCN (0.3M) | 45% | PhN(CH₃)(CH₂CH₃) 45% |
| PhN⁺(CH₃)₃ I⁻ (0.3M) | PhSiH₃ (2 eq.) | Co₂CO₈ (0.06 eq.) | CO 8 bar, 17 h, 150° C. Additive: N-ethyl-acetanilide (0.3 eq.) Solvent: MeCN (0.3M) | 53% | PhN(CH₃)(CH₂CH₃) 53% |
| PhN⁺(CH₃)₃ I⁻ (0.3M) | PhSiH₃ (2 eq.) | Co₂CO₈ (0.06 eq.) | CO 8 bar, 17 h, 100° C. Additive: N-ethyl-acetanilide (0.3 eq.) Solvent: MeCN (0.3M) | 46% | PhN(CH₃)(CH₂CH₃) 46% |
| PhN⁺(CH₃)₃ I⁻ (0.3M) | PhSiH₃ (2 eq.) | Co₂CO₈ (0.06 eq.) | CO 8 bar, 17 h, 100° C. Additive: AlCl₃ (0.3 eq.) Solvent: MeCN (0.3M) | 17% | PhN(CH₃)(CH₂CH₃) 17% |
| 1,2,3,4-tetrahydroisoquinoline NH (0.3M) | PhSiH₃ (2 eq.) | Co₂CO₈ (0.06 eq.) | CO 8 bar, 16 h, 200° C. Promoter: CH₃I (0.3 eq.) Additive: N-ethylacetanilide (0.3 eq.) Solvent: toluene (0.3M) | 40% | N-ethyl-1,2,3,4-tetrahydroisoquinoline |

The yields are determined by GC/MS. The alkylamine yields were not optimised but are encouraging. The possible by-products obtained are the corresponding amides that result from the carbonylation of the corresponding alkylamines. These amides can be recycled and can serve as starting products.

The results show that, under the operating conditions indicated in Table 4, the conversion of amines of formula (II) into alkylamine of formula (I) takes place in general with an excellent yield. This is because all the converted amine gives the corresponding alkylamine.

All the results obtained in the experimental part show that the preparation of alkylamines by the method of the invention is sufficiently flexible to effectively convert a large variety of amines into alkylamines.

The invention claimed is:

1. A method for preparing alkylamines of formula (I):

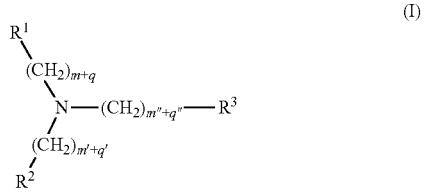

wherein:
R$^1$, R$^2$ and R$^3$ represent, independently of each other, a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted; or R$^1$ and R$^2$, taken together with the nitrogen atom to which they are bound, form a heterocycle, optionally substituted, and R$^3$ represents a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted;

m, m', m" are integers chosen from 0 and 1;

q, q', q" are integers chosen from 0, 1, 2, 3, 4, 5, 6, 7, 8, 9 and 10;

R$^1$, R$^2$ and R$^3$ and —CH$_2$— optionally comprise H, C, N, O, F and/or S as defined below:

H represents a hydrogen atom ($^1$H), deuterium ($^2$H) or tritium ($^3$H);

C represents a carbon atom ($^{12}$C), an isotope $^{11}$C, $^{13}$C or $^{14}$C;

N represents a nitrogen atom ($^{14}$N); an isotope $^{15}$N;

O represents a oxygen atom ($^{16}$O); an isotope $^{17}$O or $^{18}$O;

F represents a fluorine atom ($^{19}$F), an isotope $^{18}$F;

S represents a sulphur atom ($^{32}$S), an isotope $^{33}$S, $^{34}$S or $^{36}$S;

characterised by reacting an amine of formula (II)

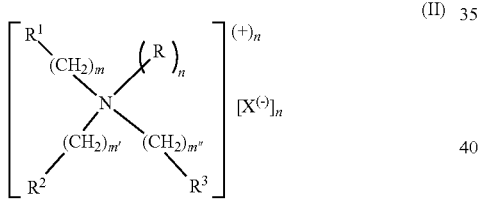

(II)

wherein
R$^1$, R$^2$ and R$^3$, —CH$_2$—, m, m' and m" are as defined above;

R represents a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted;

X represents a halogen atom, trifluoromethylsulfonate (triflate), methanesulfonate (mesylate), p-toluenesulfonic acid (tosylate);

n is an integer chosen from 0 and 1;

with CO wherein C and O are as defined above and a reducing agent chosen from H$_2$, LiAlH$_4$, NaBH$_4$, Zn, LiBH$_4$, a silane of formula (III)

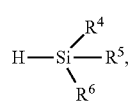

(III)

and
a borane of formula (IV)

(IV)

wherein
R$^4$, R$^5$, R$^6$, R$^7$ and R$^8$ represent, independently of each other, a hydrogen atom, an alkyl group, an alkoxy group, an alkenyl group, an alkynyl group, an aryl group, a heteroaryl group, a heterocycle, a silyl group, a siloxy group, an amino group, said alkyl, alkenyl, alkynyl, aryl, heteroaryl, heterocycle, silyl, siloxy and amino groups being optionally substituted; or R$^7$ and R$^8$ taken together with the boron atom to which they are bound form a heterocycle, optionally substituted;

in the presence of a metal catalyst, and optionally a promoter;

wherein the catalyst is a metal salt wherein
the metal is a transition metal chosen from chromium, tungsten, manganese, rhenium, silver, ruthenium, rhodium, cobalt, iron, nickel, copper, iridium, osmium, molybdenum, gold, platinum and palladium, and the anions forming the salts with the aforementioned transition metals are chloride (Cl$^-$), sulphate (SO$_4^{2-}$), sulphide (S$^{2-}$), nitrate (NO$_3^-$), oxide (O$^{2-}$) and hydroxide (OH$^-$); with the substitution on alkyl, alkenyl and alkynyl groups being one or more hydroxyl groups, one or more alkoxy groups, one or more aryl groups, one or more halogen atoms chosen from fluorine, chlorine, bromine and iodine atoms, one or more nitro groups (—NO$_2$), one or more nitrile groups (—CN), one or more alkyl groups, the substitution on heteroaryl and heterocycle groups being one or more hydroxyl groups, one or more alkoxy groups, one or more aryl groups, one or more halogen atoms chosen from fluorine, chlorine, bromine and iodine atoms, one or more nitro groups (—NO$_2$), one or more nitrile groups (—CN), one or more alkyl groups, and the substitution on aryl groups being one or more hydroxyl groups, one or more alkoxy groups, one or more siloxy groups, one or more halogen atoms chosen from fluorine, chlorine, bromine and iodine atoms, one or more nitro groups (—NO$_2$), one or more nitrile groups (—CN), one or more alkyl groups.

2. A method for preparing alkylamines of formula (I):

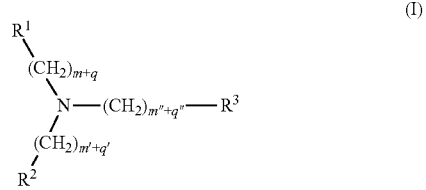

(I)

wherein:
R$^1$, R$^2$ and R$^3$ represent, independently of each other, a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted; or
R$^1$ and R$^2$, taken together with the nitrogen atom to which they are bound, form a heterocycle, optionally substituted, and
R$^3$ represents a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted;
m, m', m" are integers chosen from 0 and 1;
q, q', q" are integers chosen from 0, 1, 2, 3, 4, 5, 6, 7, 8, 9 and 10;
R$^1$, R$^2$ and R$^3$ and —CH$_2$— optionally comprise H, C, N, O, F and/or S as defined below:
H represents a hydrogen atom ($^1$H), deuterium ($^2$H) or tritium ($^3$H);
C represents a carbon atom ($^{12}$C) an isotope $^{11}$C, $^{13}$C or $^{14}$C;
N represents a nitrogen atom ($^{14}$N), an isotope $^{15}$N;
O represents an oxygen atom ($^{16}$O), an isotope $^{17}$O or $^{18}$O;
F represents a fluorine atom ($^{19}$F), an isotope $^{18}$F;
S represents a sulphur atom ($^{32}$S), an isotope $^{33}$S, $^{34}$S or $^{36}$S;
characterised by reacting an amine of formula (II)

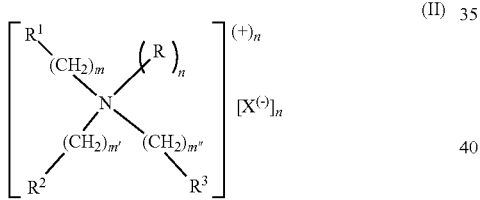

(II)

wherein
R$^1$, R$^2$ and R$^3$, —CH$_2$—, m, m' and m" are as defined above;
R represents a hydrogen atom, an alkyl group, an alkenyl group, an alkynyl group, an aryl group, a heteroaryl group, a heterocycle, said alkyl, alkenyl, alkynyl, aryl, heteroaryl, heterocycle groups being optionally substituted;
X represents a halogen atom, trifluoromethylsulfonate (triflate), methanesulfonate (mesylate), p-toluenesulfonic acid (tosylate);
n is an integer chosen from 0 and 1;
with CO wherein C and O are as defined above and a reducing agent chosen from H$_2$, LiAlH$_4$, NaBH$_4$, Zn, LiBH$_4$,
a silane of formula (III)

(III)

and
a borane of formula (IV)

(IV)

wherein
R$^4$, R$^5$, R$^6$, R$^7$ and R$^8$ represent, independently of each other, a hydrogen atom, an alkyl group, an alkoxy group, an alkenyl group, an alkynyl group, an aryl group, a heteroaryl group, a heterocycle, a silyl group, a siloxy group, an amino group, said alkyl, alkenyl, alkynyl, aryl, heteroaryl, heterocycle, silyl, siloxy and amino groups being optionally substituted; or
R$^7$ and R$^8$ taken together with the boron atom to which they are bound form a heterocycle, optionally substituted;
in the presence of a metal catalyst, and optionally a promoter;
wherein the catalyst is a metal complex wherein
the metal is a transition metal chosen from chromium, tungsten, manganese, rhenium, silver, ruthenium, rhodium, cobalt, iron, nickel, copper, iridium, osmium, molybdenum, gold, platinum and palladium, and
the ligands being bound to the transition metals are chosen from:
nitrogenous bases chosen from trimethylamine, triethylamine, piperidine, 4-dimethylaminopyridine (DMAP), 1,4-diazabicyclo[2.2.2]octane (DABCO), proline, phenylalanine, a thiazolium salt, N-diisopropylethylamine (DIPEA or DIEA), bipyridyl (bipy), terpyridine (terpy); phenanthroline (phen), ethylenediamine, N,N,N',N'-tetra-methyl-ethylenediamine (TMEDA), quinoline and pyridine;
phosphorous bases chosen from triphenylphosphine, 2,2'-bis(diphenylphosphino)-1,1'-binaphthyl (BINAP), triisopropylphosphine, tris[2-diphenylephosphino)ethyl]phosphine (PP$_3$), tricyclohexylphosphine, 1,2-bis-diphenylphosphinoethane (dppe), 1,2-bis(diphenylphosphino)ethane (dppb); alkyl and aryl phosphonates chosen from diphenylphosphate, triphenylphosphate (TPP), tri(isopropylphenyl)phosphate (TIPP), cresyldiphenyl phosphate (CDP), tricresylphosphate (TCP); alkyl and aryl phosphates chosen from di-n-butylphosphate (DBP), tris-(2-ethylhexyl)-phosphate and triethyl phosphate;
oxygenated bases chosen from acetate (OAc), acetylacetonate, methanolate, ethanolate, benzoyl peroxide;
silylated ligands chosen from triphenylsilyl, diphenylhydrosilyl, trimethylsilyl, dimethylhydrosilyl, triethylsilyl, triethoxysilyl;
carbonaceous ligands chosen from CO, CN$^-$, and N-heterocyclic carbenes from an imidazolium salt chosen from the salts of 1,3-bis(2,6-diisopropylphenyl)-1H-imidazol-3-ium, 1,3-bis(2,6-diisopropylphenyl)-4,5-dihydro-1H-imidazol-3-ium, 1,3-bis(2,4,6-trimethylphenyl)-1H-imidazol-3-ium, 1,3-bis(2,4,6-trimethylphenyl)-4,5-dihydro-1H-imidazol-3-ium, 4,5-dichloro-1,3-bis(2,6-diisopropylphenyl)-1H-imidazol-3-ium, 1,3-di-tert-butyl-1H-imidazol- 3-ium, 1,3-di-tert-butyl-4,5-dihydro-1H-imidazol-3-ium, said salts being in the form of chloride salts;
the metal complex optionally comprising a counterion chosen from sodium ($Na^+$), potassium ($K^+$), ammonium ($NH_4^+$); with
the substitution on alkyl, alkenyl and alkynyl groups being one or more hydroxyl groups, one or more alkoxy groups, one or more aryl groups, one or more halogen atoms chosen from fluorine, chlorine, bromine and iodine atoms, one or more nitro groups (—$NO_2$), one or more nitrile groups (—CN), one or more alkyl groups,
the substitution on heteroaryl and heterocycle groups being one or more hydroxyl groups, one or more alkoxy groups, one or more aryl groups, one or more halogen atoms chosen from fluorine, chlorine, bromine and iodine atoms, one or more nitro groups (—$NO_2$), one or more nitrile groups (—CN), one or more alkyl groups, and
the substitution on aryl groups being one or more hydroxyl groups, one or more alkoxy groups, one or more siloxy groups, one or more halogen atoms chosen from fluorine, chlorine, bromine and iodine atoms, one or more nitro groups (—$NO_2$), one or more nitrile groups (—CN), one or more alkyl groups.

3. The method according to claim 1, wherein
$R^1$, $R^2$ and $R^3$ represent, independently of each other, a hydrogen atom, an alkyl group, an aryl group, a heteroaryl group, a heterocycle, said alkyl, aryl, heteroaryl, heterocycle groups being optionally substituted as defined in claim 1;
m, m' and m" are integers chosen from 0 and 1;
q, q', q" are integers chosen from 0, 1, 2, 3, 4, 5, 6, 7, 8, 9 and 10;
n=0.

4. The method according to claim 1, wherein
$R^1$ and $R^2$, taken together with the nitrogen atom to which they are bound, form a heterocycle, optionally substituted as defined in claim 1, and
$R^3$ represents a hydrogen atom, an alkyl group, an aryl group, a heteroaryl group, a heterocycle, said alkyl, aryl, heteroaryl, heterocycle groups optionally being substituted as defined in claim 1;
m, m' and m" are integers chosen from 0 and 1;
q, q', q" are integers chosen from 0, 1, 2, 3, 4, 5, 6, 7, 8, 9 and 10;
n=0.

5. The method according to claim 1, wherein
$R^1$, $R^2$ and $R^3$ represent, independently of each other, a hydrogen atom, an alkyl group, an aryl group, a heteroaryl group, a heterocycle, said alkyl, aryl, heteroaryl, heterocycle groups being optionally substituted as defined in claim 1;
R represents a hydrogen atom, an alkyl group, an aryl group, a heteroaryl group, a heterocycle, said alkyl, aryl, heteroaryl, heterocycle groups being optionally substituted as defined in claim 1;
m, m' and m" are integers chosen from 0 and 1;
q, q', q" are integers chosen from 0, 1, 2, 3, 4, 5, 6, 7, 8, 9 and 10;
n=1;
X represents a halogen atom, trifluoromethylsulfonate (triflate), methanesulfonate (mesylate), p-toluenesulfonic acid (tosylate).

6. The method according to claim 1, wherein
$R^1$ and $R^2$, taken together with the nitrogen atom to which they are bound, form a heterocycle, optionally substituted as defined in claim 1, and $R^3$ represents a hydrogen atom, an alkyl group, an aryl group, a heteroaryl group, a heterocycle, said alkyl, aryl, heteroaryl, heterocycle groups being optionally substituted as defined in claim 1;
R represents a hydrogen atom, an alkyl group, an aryl group, a heteroaryl group, heterocycle, said alkyl, aryl, heteroaryl, heterocycle groups being optionally substituted as defined in claim 1;
m, m' and m" are integers chosen from 0 and 1;
q, q', q" are integers chosen from 0, 1, 2, 3, 4, 5, 6, 7, 8, 9 and 10;
n=1;
X represents a halogen atom, trifluoromethylsulfonate (triflate), methanesulfonate (mesylate), p-toluenesulfonic acid (tosylate).

7. The method according to claim 1, wherein the values of m, m', m", q, q' and q" in the alkylamines of formula (I) are chosen so that:
0≤m+q≤10; and/or
0≤m'+q'≤10; and/or
0≤m"+q"≤10.

8. The method according to claim 1, wherein the reducing agent is chosen from Hz, a silane of formula (III)

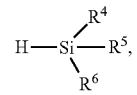

and
a borane of formula (IV)

wherein
$R^4$, $R^5$, $R^6$, $R^7$ and $R^8$ represent, independently of each other, a hydrogen atom, an alkyl group, an alkoxy group, an alkenyl group, an alkynyl group, an aryl group, a heteroaryl group, a heterocycle, a silyl group, a siloxy group, an amino group, said alkyl, alkenyl, alkynyl, aryl, heteroaryl, heterocycle, silyl, siloxy and amino groups being optionally substituted as defined in claim 1; or
$R^7$ and $R^8$, taken together with the boron atom to which they are bound, form an optionally substituted heterocycle, the substitution being as defined in claim 1.

9. The method according to claim 1, wherein the promoter is of formula RX, with R representing a hydrogen atom, an alkyl group, an aryl group, a heteroaryl group, a heterocycle, said alkyl, aryl, heteroaryl, heterocycle groups being optionally substituted as defined in claim 1; and X representing a halogen atom, trifluoromethylsulfonate (triflate), methanesulfonate (mesylate), p-toluenesulfonic acid (tosylate).

10. The method according to claim 2, wherein
$R^1$, $R^2$ and $R^3$ represent, independently of each other, a hydrogen atom, an alkyl group, an aryl group, a heteroaryl group, a heterocycle, said alkyl, aryl, heteroaryl, heterocycle groups being optionally substituted as defined in claim 2;
m, m' and m" are integers chosen from 0 and 1;
q, q', q" are integers chosen from 0, 1, 2, 3, 4, 5, 6, 7, 8, 9 and 10;
n=0.

11. The method according to claim 1, wherein
$R^1$ and $R^2$, taken together with the nitrogen atom to which they are bound, form a heterocycle, optionally substituted as defined in claim 1, and
$R^3$ represents a hydrogen atom, an alkyl group, an aryl group, a heteroaryl group, a heterocycle, said alkyl, aryl, heteroaryl, heterocycle groups optionally being substituted as defined in claim 1;
m, m' and m" are integers chosen from 0 and 1;
q, q', q" are integers chosen from 0, 1, 2, 3, 4, 5, 6, 7, 8, 9 and 10;
n=0.

12. The method according to claim 2, wherein
$R^1$, $R^2$ and $R^3$ represent, independently of each other, a hydrogen atom, an alkyl group, an aryl group, a heteroaryl group, a heterocycle, said alkyl, aryl, heteroaryl, heterocycle groups being optionally substituted as defined in claim 2;
R represents a hydrogen atom, an alkyl group, an aryl group, a heteroaryl group, a heterocycle, said alkyl, aryl, heteroaryl, heterocycle groups being optionally substituted as defined in claim 2;
m, m' and m" are integers chosen from 0 and 1;
q, q', q" are integers chosen from 0, 1, 2, 3, 4, 5, 6, 7, 8, 9 and 10;
n=1;
X represents a halogen atom, trifluoromethylsulfonate (triflate), methanesulfonate (mesylate), p-toluenesulfonic acid (tosylate).

13. The method according to claim 2, wherein
$R^1$ and $R^2$, taken together with the nitrogen atom to which they are bound, form a heterocycle, optionally substituted as defined in claim 2, and
$R^3$ represents a hydrogen atom, an alkyl group, an aryl group, a heteroaryl group, a heterocycle, said alkyl, aryl, heteroaryl, heterocycle groups being optionally substituted as defined in claim 2;
R represents a hydrogen atom, an alkyl group, an aryl group, a heteroaryl group, heterocycle, said alkyl, aryl, heteroaryl, heterocycle groups being optionally substituted as defined in claim 2;
m, m' and m" are integers chosen from 0 and 1;
q, q', q" are integers chosen from 0, 1, 2, 3, 4, 5, 6, 7, 8, 9 and 10;
n=1;
X represents a halogen atom, trifluoromethylsulfonate (triflate), methanesulfonate (mesylate), p-toluenesulfonic acid (tosylate).

14. The method according to claim 2, wherein the values of m, m', m", q, q' and q" in the alkylamines of formula (I) are chosen so that:
$0 \leq m+q \leq 10$; and/or
$0 \leq m'+q' \leq 10$; and/or
$0 \leq m''+q'' \leq 10$.

15. The method according to claim 2, wherein the reducing agent is chosen from $H_2$, a silane of formula (III)

$$H-Si\begin{matrix}R^4\\R^5,\\R^6\end{matrix} \quad (III)$$

and
a borane of formula (IV)

$$\begin{matrix}R^8\\\phantom{x}\diagdown\\\phantom{xx}B-H\\\phantom{x}\diagup\\R^7\end{matrix} \quad (IV)$$

wherein
$R^4$, $R^5$, $R^6$, $R^7$ and $R^8$ represent, independently of each other, a hydrogen atom, an alkyl group, an alkoxy group, an alkenyl group, an alkynyl group, an aryl group, a heteroaryl group, a heterocycle, a silyl group, a siloxy group, an amino group, said alkyl, alkenyl, alkynyl, aryl, heteroaryl, heterocycle, silyl, siloxy and amino groups being optionally substituted as defined in claim 2; or
$R^7$ and $R^8$, taken together with the boron atom to which they are bound, form an optionally substituted heterocycle, the substitution being as defined in claim 2.

16. The method according to claim 2, wherein the promoter is of formula RX, with R representing a hydrogen atom, an alkyl group, an aryl group, a heteroaryl group, a heterocycle, said alkyl, aryl, heteroaryl, heterocycle groups being optionally substituted as defined in claim 2; and X representing a halogen atom, trifluoromethylsulfonate (triflate), methanesulfonate (mesylate), p-toluenesulfonic acid (tosylate).

17. The method according to claim 1, wherein the method further takes place in the presence of an additive chosen from aromatic amides chosen from acetanilide, benzanilide and N-methylacetanilide; Lewis acids chosen from $AlCl_3$, LiCl, $LiBF_4$, $FeCl_3$, $InCl_3$, $BiCl_3$.

18. The method according to claim 2, wherein the method further takes place in the presence of an additive chosen from aromatic amides chosen from acetanilide, benzanilide and N-methylacetanilide; Lewis acids chosen from $AlCl_3$, LiCl, $LiBF_4$, $FeCl_3$, $InCl_3$, $BiCl_3$.

* * * * *